United States Patent
Bae et al.

(10) Patent No.: US 7,309,750 B2
(45) Date of Patent: Dec. 18, 2007

(54) CYANOADAMANTYL COMPOUNDS AND POLYMERS

(75) Inventors: Young C. Bae, Worcester, MA (US); Robert J. Kavanagh, Natick, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 11/075,545

(22) Filed: Mar. 8, 2005

(65) Prior Publication Data
US 2005/0208418 A1 Sep. 22, 2005

Related U.S. Application Data

(60) Provisional application No. 60/551,880, filed on Mar. 9, 2004.

(51) Int. Cl.
*C08F 10/00* (2006.01)
*G03F 7/004* (2006.01)

(52) U.S. Cl. .................... 526/282; 430/270.1; 430/905; 430/910

(58) Field of Classification Search ............ 430/270.1, 430/905, 910; 526/282
See application file for complete search history.

(56) References Cited

U.S. PATENT DOCUMENTS

| | | | | |
|---|---|---|---|---|
| 5,399,647 | A * | 3/1995 | Nozaki ................ | 430/270.1 |
| 6,635,401 | B2 | 10/2003 | Li et al. | |
| 6,692,888 | B1 | 2/2004 | Barclay et al. | |
| 2002/0155379 | A1 | 10/2002 | Yoon et al. ............ | 430/270.1 |
| 2003/0203309 | A1* | 10/2003 | Nishimura et al. ...... | 430/270.1 |
| 2003/0235781 | A1 | 12/2003 | Shida et al. ............ | 430/270.1 |
| 2005/0208417 | A1 | 9/2005 | Bae et al. | |
| 2006/0167302 | A1 | 7/2006 | Ito et al. | |
| 2006/0186160 | A1 | 8/2006 | Hubbe et al. | |

FOREIGN PATENT DOCUMENTS

| | | |
|---|---|---|
| DE | 43 19 178 | 7/1993 |
| EP | 1 091 249 | 4/2001 |
| EP | 1 225 480 | 7/2002 |
| JP | 2003-122007 | 4/2003 |
| JP | 2004-029542 | 1/2004 |

OTHER PUBLICATIONS

Database CA 'Online Chemical Abstracts Service, Columbus, OH, Shida, et al, "High molecular compounds for photoresists, monomeric compounds, photosensitive resin compositions, method for forming patterns with the compositions, and process for production of electronic components," XP002339261, retrieved from STN database accession No. 136:377479 (abstract) no date.

Database CA 'Online', Chemical abstracts Service, Columbus, OH, Yoon, et al, "Photosensitive monomers with acid decomposable protective group containing lactone groups, photosensitive polymers, and chemical amplified photoresist compositions," XP002339260 retrieved from STN database accession No. 137:317938 *abstract* no date.

Database CA 'Online', Chemical abstracts Service, Columbus, OH, Fujimori, Toru: "Positive chemically amplified resist compositions having improved edge roughness of patterns and high sensitivity", XP002339259 retrieved from STN database accession No. 138:346480 *abstract* no date.

Database CA 'Online', Chemical abstracts service, Columbus, OH, Sato, et al, "Positive photoresist compositions with high and uniform resolution and good tolerance to side lobe radiation for far UV", XP002339258 retrieved from STN database accession No. 139:28624 *abstract* no date.

* cited by examiner

*Primary Examiner*—John S. Chu
(74) *Attorney, Agent, or Firm*—Peter F. Corless; Darryl P. Frickey; Edwards Angell Palmer Dodge, LLP

(57) ABSTRACT

Cyanoadamantyl compounds, polymers that comprise polymerized units of such compounds, and photoresist compositions that comprise such polymers are provided. Preferred polymers of the invention are employed in photoresists imaged at wavelengths less than 250 nm such as 248 nm and 193 nm.

12 Claims, No Drawings

CYANOADAMANTYL COMPOUNDS AND POLYMERS

The present application claims the benefit of U.S. provisional application No. 60/551,880, filed Mar. 9, 2004, which is incorporated herein by reference in its entirety.

BACKGROUND OF THE INVENTION

1. Field of the Invention

The present invention relates to cyanoadamantyl compounds, polymers that comprise polymerized units of such compounds, and photoresist compositions that comprise such polymers. Preferred polymers of the invention have at least one or two distinct repeat units in addition to cyanoadamantyl units and are employed in photoresists imaged at wavelengths less than 250 nm such as 248 nm and 193 nm.

2. Background

Photoresists are photosensitive films used for transfer of images to a substrate. A coating layer of a photoresist is formed on a substrate and the photoresist layer is then exposed through a photomask to a source of activating radiation. The photomask has areas that are opaque to activating radiation and other areas that are transparent to activating radiation. Exposure to activating radiation provides a photoinduced chemical transformation of the photoresist coating to thereby transfer the pattern of the photomask to the photoresist-coated substrate. Following exposure, the photoresist is developed to provide a relief image that permits selective processing of a substrate.

While currently available photoresists are suitable for many applications, current resists also can exhibit significant shortcomings, particularly in high performance applications such as formation of highly resolved sub-quarter micron and even sub-tenth micron features.

Consequently, interest has increased in photoresists that can be photoimaged with short wavelength radiation, including exposure radiation of below 200 nm such as 193 nm.

Polymers that contain alicyclic groups such as norbornyl are of interest as resin components for photoresists imaged at sub-200 nm wavelengths due to the relatively low absorption of such resins to exposure radiation. See U.S. Pat. No. 6,509,134; T. Wallow et al., Proc. SPIE 2724 (1996) 334; S. J. Choi, et al., J. Photopolymer Sci. Technology, 10 (1997) 521; S. J. Choi et al., Proc. SPIE 3999 (2000) 54; U.S. Pat. Nos. 5,843,624; 6,306,554; and 6,517,990; and Japanese Published Application 2003-12207.

Efforts to enhance transparency for short wavelength exposure can negatively impact other important performance properties such as substrate adhesion and resistance to etchants employed after development, which in turn can dramatically compromise image resolution. In particular, reducing aromatic (e.g. phenyl or substituted phenyl such as phenol) content of a resist to thereby increase transparency at sub-200 nm exposures can provide a resist that exhibits any of poor resistance to plasma etchants used to process substrate surfaces bared upon development, poor adhesion to an underlying substrate, and poor (narrow) lithographic processing windows. See, for instance, U.S. Pat. No. 6,479,211.

Various efforts have been made to improve performance of such short-wavelength photoresists. Certain use of photoresist resins that have certain cyano substitution has been reported. See U.S. Published Applications 2003/0186160 and 2003/0008502; and Japanese Published Applications 2003-122007 and 2004-29542. Highly useful photoresists that comprise a resin with cyano groups are disclosed in U.S. Pat. No. 6,692,888 assigned to the Shipley Company.

It thus would be desirable to have new photoresist compositions, particularly resist compositions that can be effectively imaged at short wavelengths such as sub-250 nm exposure wavelengths.

SUMMARY OF THE INVENTION

We now provide new cyano-substituted adamantyl compounds and polymers that comprise polymerized units of such compounds. We further provide photoresists that comprise such cyanoadamantyl polymers. Photoresists of the invention can offer notably improved performance properties, including enhanced lithographic processing windows, substrate adhesion and resistance to plasma etchants.

The term "cyanoadamantyl compound", "cyano-substituted adamantyl compound" or other similar term as referred to herein refers to a compound that comprises an adamantyl group and the adamantyl ring is substituted by a cyano moiety or a group that comprises a cyano moiety such as cyanoalkyl (e.g. —($C_{1-8}$alkyl)CN) and the like. For many applications, preferred are compounds where a cyano moiety is not directly covalently linked to an adamantyl ring carbon atom, but is spaced from an adamantyl ring atom by one, two, three, four or more atoms such as through a cyanoalkyl group. Such spaced cyano moieties that are covalently linked to an adamantyl ring through one or more interposed atoms are generally referred to as a cyano group that is pendant to the adamantyl ring.

Preferred cyanoadamantyl compounds of the invention further comprise a functionality that can enable polymerization of the compound. Typically, the cyanoadamantyl compound will comprise an unsaturated moiety, such as a carbon-carbon double bond.

Particularly preferred cyanoadamantyl compounds are acrylate esters, with a cyanoadamantyl moiety comprising at least a portion of the ester group.

More specifically, preferred cyanoadamantyl compounds of the invention include those of the following Formula I:

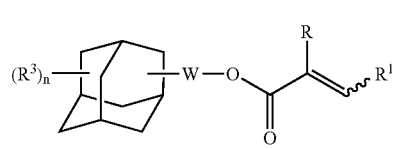

wherein R and $R^1$ are each hydrogen or alkyl, and R and $R^1$ are preferably hydrogen or methyl;

each $R^3$ is independently cyano, hydroxy, optionally substituted alkyl including cyanoalkyl, or optionally substituted heteroalkyl including cyanoheteroalkyl, with at least one $R^3$ being cyano, optionally substituted cyanoalkyl or optionally substituted cyanoheteroalkyl;

W is a chemical bond or a group that comprises a quaternary carbon linked to the ester oxygen, e.g. —C(CH$_3$)$_2$—; and n is an integer of 1 to 4, more typically n is 1, 2 or 3.

For polymers used for positive-acting photoresist compositions, preferably the cyanoadamantyl moiety provides a quaternary acrylate ester to facilitate photoacid-induced cleavage of the ester. Reference to a "quaternary cyanoadamantyl ester group" or other similar term indicates that a quaternary carbon of the group comprises an adamantyl moiety and is covalently linked to the ester oxygen, i.e.

—C(=O)O-TR where T is a quaternary (fully substituted by other than hydrogen) carbon of a group R that comprises a cyanoadamantyl moiety. In at least many cases, preferably a quaternary ring carbon of the adamantyl moiety will be covalently linked to the ester oxygen, such as exemplified by compounds of the below Formulae II, IIa, III and IIIa. However, the quaternary carbon linked to the ester oxygen also can be exocyclic to the adamantyl ring, typically where the adamantyl ring is one of the substituents of the exocyclic quaternary carbon, such as exemplified by compounds of Formula IV and IVa below.

Polymers of the invention are preferably adapted for use in photoresists imaged at 248 nm and 193 nm.

For example, for use in 248 nm photoresists, a polymer of the invention preferably contains aromatic groups, particularly phenyl groups such as phenolic units. A copolymer or terpolymer that comprises polymerized units of vinylphenol and a cyanoadamantyl acrylate ester can be preferred for use in photoresists imaged at 248 nm.

For use in 193 run photoresists, a polymer of the invention preferably will be at least substantially free of aromatic groups such as phenyl. Preferred polymers for use in 193 nm photoresists will contain less than about 5 mole percent aromatic groups, more preferably less than about 1 mole percent aromatic groups, more preferably less than about 0.1, 0.02, 0.04 and 0.08 mole percent aromatic groups and still more preferably less than about 0.01 mole percent aromatic groups. Particularly preferred polymers for use in 193 nm photoresists will be completely free of aromatic groups. Aromatic groups can be highly absorbing of sub-200 nm radiation and thus are undesirable for polymers used in photoresists imaged with such short wavelength radiation.

Also, preferred polymers of the invention, including polymers that are adapted for imaged at 248 nm and 193 nm, will be at least substantially free of fluorine atoms, or in another aspect at least substantially free of any halogen atoms. Particularly preferred polymers will be completely free of fluorine atoms, or in another aspect completely free of any halogen atoms. A polymer that is at least substantially free of fluorine atoms or halogen atoms contains less than 2 or 3 number percent of fluorine or halogen atoms based on the total number of atoms in the polymer, more preferably less than 0.5, 1 or 2 number percent of fluorine or halogen atoms based on the total number of atoms in the polymer.

Polymers of the invention may contain units in addition to cyanoadamantyl group. For example, dissolution enhancers may be included in a polymer of the invention, such as anhydrides and lactones, e.g. polymerized maleic anhydride, itaconic anhydride, and/or α-butyrolactone. Contrast enhancing groups also may be present in polymers of the invention, such as groups provided by polymerization of methacrylic acid, acrylic acid, and such acids protected as photoacid labile esters, e.g. as provided by reaction of ethoxyethyl methacrylate, t-butoxy methacrylate, t-butylmethacrylate and the like. Polymer groups that can provide resistance to plasma etchants also are preferred. For instance, for polymers used in photoresists imaged at 248 nm, it can be preferred to include polymerized styrene units, which can enhance etch resistance. For polymers used in photoresists imaged at 193 nm, it maybe preferable to include polymerized norbornene groups and other polymerized units that contain alicyclic groups including both carbon alicyclic groups and heteroalicyclic groups. As referred to herein, the term "carbon alicyclic group" means each ring member of the non-aromatic group is carbon. The carbon alicyclic group can have one or more endocyclic carbon-carbon double bonds, provided the ring is not aromatic.

Preferred for many resist applications are polymers of the invention that comprise repeat units that contain moieties that comprise one more hetero atoms (particularly N, O or S, preferably O or S) such as may be present as a component of an alcohol, alkylsulfide, lactone, ester, and the like. Such hetero-containing groups suitably will be distinct from photoacid-labile moieties of a polymer (e.g. photoacid-labile ester or acetal groups), i.e. these hetero groups will not undergo cleavage reactions during typical lithographic exposure and post-exposure bake treatments.

Such hetero-containing groups also may be an oxygen- and/or sulfur-containing heteroalicyclic ring that is preferably fused to the polymer backbone (i.e. at least two heteroalicyclic ring atoms as part of the polymer backbone). The heteroalicyclic ring has one or more oxygen and/or sulfur atoms as ring members. Many preferred fused heteroalicyclic groups will be other than lactones or anhydride, or otherwise will not contain a keto carbon (i.e. >C=O) as a member of the alicyclic ring. For instance, preferred are groups that may be provided by an optionally substituted 3,4-dihydro-2-H-pyran including e.g. 3,4-dihydro-2-methoxy-2-H-pyran, 3,4-dihydro-2-ethoxy-2-H-pyran, 3,4-dihydro-2-propoxy-2-H-pyran, and the like.

By stating herein that a cyclic group (e.g. a carbon alicyclic or heteroalicyclic group) is fused to a polymer backbone, it is meant that two ring members of the cyclic group, typically two adjacent carbon atoms of the cyclic group, are also part of the polymer backbone. Such a fused ring can be provided by polymerizing a cyclic monomer that has an endocyclic double bond, e.g. by polymerizing an optionally substituted norbornene group, optionally substituted 3,4-dihydro-2-H-pyran or other vinyl alicyclic group.

The invention also provides methods for forming relief images, including methods for forming a highly resolved relief image such as a pattern of lines where each line has essentially vertical sidewalls and a line width of about 0.25 microns or less, and even a width of about 0.10 microns or less. The invention also includes methods for manufacture of an electronic device article such as a processed microelectronic semiconductor wafer through application and imaging of a photoresist of the invention. The invention further provides articles of manufacture comprising substrates such as a microelectronic wafer substrate having coated thereon a polymer, photoresist or resist relief image of the invention.

Other aspects of the invention are disclosed infra.

DETAILED DESCRIPTION OF THE INVENTION

As discussed above, we now provide new cyano-substituted adamantyl compounds and polymers that comprise polymerized units of such compounds.

Preferred compounds and polymers of the invention comprise one or more adamantyl moieties that contain a cyano moiety-ring substituent, where the cyano (—C≡N) functionality itself is not directly covalently linked to a ring carbon of the adamantyl group, but where the cyano functionality is spaced from an adamantyl ring carbon by 1 to about 16 other atoms, more typically 1 to about 6 carbons or other atoms, i.e. cyano groups that are "pendant" or spaced by one or more interposed atoms from an adamantyl ring atoms as defined above.

Preferred compounds and polymers of the invention also include one or more adamantyl moieties where a cyano moiety-ring substituent is present on the 2 or 4 positions of an adamantyl ring, or other adamantyl ring positions that have two available valances for substitution.

As discussed above, for many resist applications, preferably compounds and polymers of the invention will be at least substantially free or completely free of fluorine atoms, or at least substantially free or completely free of any halogen atoms.

Compounds

As discussed above, preferred cyanaoadamantyl compounds of the invention further comprise a functionality that can enable polymerization of the compound. Typically, the cyanoadamantyl compound will comprise an unsaturated moiety, such as a carbon-carbon double bond, e.g. preferred are cyanoadamantyl acrylate esters.

Preferred cyanoadamantyl compounds of the invention include those of the following Formula I:

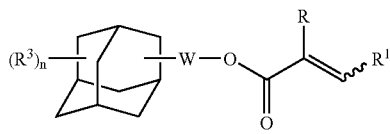

wherein R, $R^1$, $R^3$, W and n are as defined above.

As discussed above, preferred are cyanoadamantyl compounds that have cyano group (e.g. cyano, cyanoalkyl, cyanoheteroalkyl) substitution at a 2 or 4 adamantyl ring position that has two available valences for substitution, i.e. a —$CH_2$— adamantyl ring atom in the absence of any substitution.

In the case of cyanoadamantyl ester compounds of the invention, it is also preferred that a single 2 or 4 adamantyl ring position is substituted by both 1) a cyano-containing group ((e.g. cyano, cyanoalkyl, cyanoheteroalkyl) and 2) the ester moiety (i.e. —OC(=O)R).

More particularly, preferred cyanoadamantyl ester compounds of the invention include compounds of the following Formulae II and IIa:

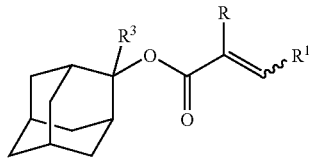

wherein in Formula II, R and $R^1$ are as defined in Formula I above, and $R^3$ is cyano, optionally substituted cyanoalkyl, or optionally substituted cyanoheteroalkyl.

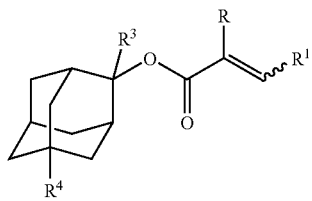

wherein in Formula IIa, R $R^1$ are each the same as defined in Formula I above; and $R^3$ and $R^4$ are each independently chosen from among cyano, hydroxy, optionally substituted alkyl including cyanoalkyl, or optionally substituted heteroalkyl including cyanoheteroalkyl, with at least one $R^3$ and $R^4$ being cyano, optionally substituted cyanoalkyl or optionally substituted cyanoheteroalkyl.

As indicated above, preferred cyanoadamantyl ester compounds of the invention include compounds methacrylate esters, such as compounds of the following Formula III and IIIa:

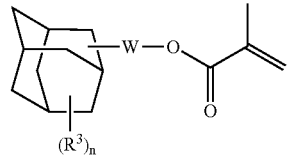

wherein in Formula III, W, each $R^3$ and n are the same as defined in Formula I above;

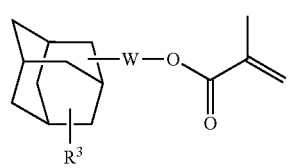

wherein in Formula IIIa, W is the same as defined in Formula I and $R^3$ is cyano, optionally substituted cyanoalkyl, or optionally substituted cyanoheteroalkyl.

As discussed, a quaternary carbon linked to an ester group oxygen suitably can be exocyclic to an adamantyl ring of a cyanoadamantyl group, i.e. where an adamantyl ring atom is not covlanetly linked directly to an ester oxygen. For instance, preferred are compounds of the following Formula IV and IVa:

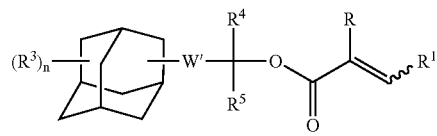

wherein in Formula IV, R, $R^1$, $R^3$ and n are the same as defined in Formula I above;

$R^4$ and $R^5$ are the same or different non-hydrogen substituents such as optionally substituted alkyl, optionally substituted carbocyclic aryl such as optionally substituted phenyl, optionally substituted heteroalkyl, and the like; and W' is a linker such as a chemical bond (i.e. W' absent), optionally substituted alkyl, optionally substituted carbocyclic aryl such as optionally substituted phenyl, optionally substituted heteroalkyl, and the like;

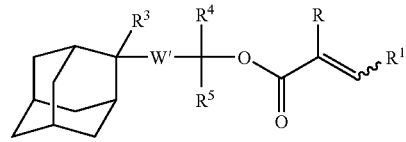

wherein in Formula IVa, R and $R^1$ are as defined in Formula I above, $R^3$ is cyano, optionally substituted cyanoalkyl, or optionally substituted cyanoheteroalkyl; and W', $R^4$ and $R^5$ are the same as defined in Formula IV above.

Specifically preferred compounds include the following:

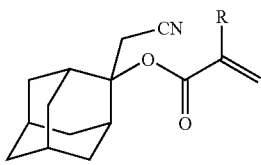

2-Methyl-acrylic acid
2-cyanomethyl-adamantan-2-yl ester

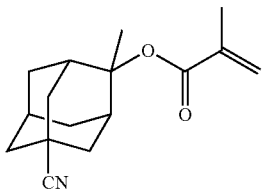

2-Methyl-acrylic acid
5-cyano-2-methyl-adamantan-2-yl ester

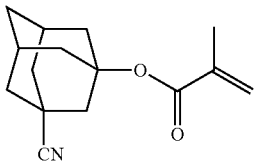

2-Methyl-acrylic acid 3-cyano-adamantan-1-yl ester

Polymers

As discussed above, preferred polymers of the invention may comprise two or more distinct repeat units, where at least one of the repeat units comprises a cyanoadamantyl group.

More particularly, preferred polymers may comprise a structure of the following Formula V:

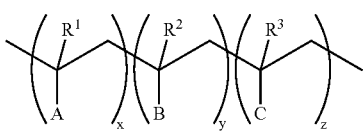

wherein at least one of A or B comprises a cyanoadamantyl group, and the other one or two polymer groups may be distinct polymer units and comprises e.g. a photoacid-labile moiety such as an acid-labile ester or acetal group; or an anhydride or lactone such as a maleic anhydride, itaconic anhydride, and/or α-butyrolactone; or other contrast-enhancing groups such polymerized units of methacrylic acid, acrylic acid; or an etch-resistance enhancing group such as polymerized optionally-substituted styrene, optionally-substituted alpha-methylstyrene, optionally-substituted norbornene; or other polymerized esters that comprise an alicyclic group; and the like;

$R^1$, $R^2$ and $R^3$ are each independently hydrogen or optionally substituted $C_{1-6}$alkyl, and preferably $R^1$, $R^2$ and $R^3$ are each independently hydrogen or methyl; and x, y and z are mole percents of the respective repeat units based on total polymers units and x and y are each greater than zero and z can be zero (where the C repeat unit is not present in the polymer) or greater than zero (where the C repeat unit is present in the polymer).

As discussed above, preferred are cyanoadamantyl ester compounds and polymers that contain polymerized groups of such esters. For instance, preferred are polymers that comprise a structure of the a structure of the following Formula VI:

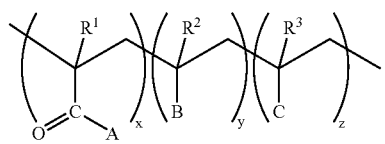

wherein A is a cyanoadamantyl group, and B, C, $R^1$, $R^2$, $R^3$, x, y, and z are each the same as defined in Formula V above.

As also discussed above, polymers of the invention may comprise a variety of groups distinct from cyanoadamantyl groups.

Thus, for example, polymers of the invention may comprise photoacid-labile groups that do not contain a cyanoadamantyl group. Preferred are t-butyl esters as well as carbon alicyclic photoacid labile ester groups. Preferred alicyclic groups of such esters will have a molecular volume of at least about 125 or about 130 Å$^3$, more preferably a molecular volume of at least about 140 or 160 Å$^3$. Alicyclic groups larger than about 220 or 250 Å$^3$ may be less preferred, in at least some applications. References herein to molecular volumes designate volumetric size as determined by standard computer modeling, which provides optimized chemical bond lengths and angles. A preferred computer program for determining molecular volume as referred to herein is Alchemy 2000, available from Tripos. For a further discussion of computer-based determination of molecular size, see T Omote et al, *Polymers for Advanced Technologies*, volume 4, pp. 277-287.

Particularly preferred quaternary alicyclic groups of photoacid-labile units include the following, where the wavy line depicts a bond to the carboxyl oxygen of the ester group, and R is suitably optionally substituted alkyl, particularly $C_{1-8}$alkyl such as methyl, ethyl, etc.

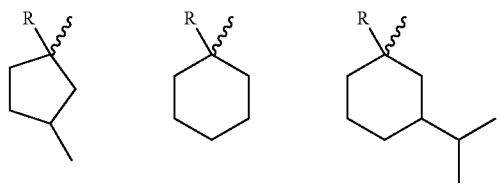

-continued

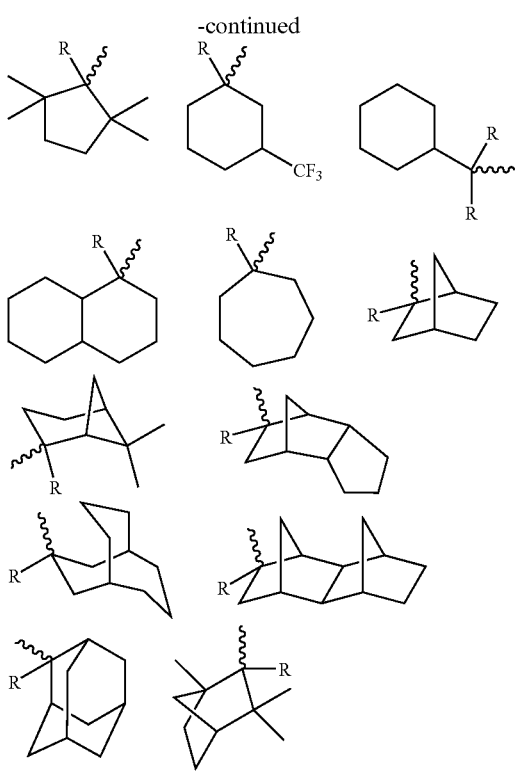

Suitable photoacid-labile groups also will include acetal groups such as may be provided by reaction of a vinyl ether such as ethyl vinyl ether with a hydroxy or carboxy group.

Polymers of the invention also may contain heteroalkyl groups, which may preferably fused to a polymer backbone often in combination with a carbon alicyclic group such as a polymerized optionally substituted norbornene. Such fused heteroalicyclic groups also are disclosed in U.S. Pat. No. 6,306,354 assigned to the Shipley Company.

Preferred polymers of the invention that contain oxygen heteroalicyclic units may comprise a structure of the following Formula I:

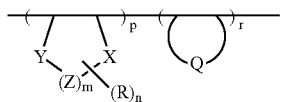

wherein X, Y, and each Z are each independently carbon or oxygen, with at least one of X, Y or Z being oxygen, and preferably no more than two of X, Y and Z being oxygen;

Q represents an optionally substituted carbon alicyclic ring such as norbornyl fused to the polymer backbone (i.e. two Q ring members being adjacent carbons of the polymer backbone); the alicyclic ring suitably having from about 5 to about 18 carbon atoms and is suitably a single ring (e.g. cyclopentyl, cyclohexyl or cycloheptyl), or more preferably Q is polycyclic e.g. and contain 2, 3, 4 or more bridged, fused or otherwise linked rings, and preferred substituents of a substituted Q group include photoacid-labile moieties such as a photoacid-labile ester;

each R is the same or different non-hydrogen substituent such as cyano; optionally substituted alkyl preferably having 1 to about 10 carbon atoms; optionally substituted alkanoyl preferably having 1 to about 10 carbon atoms; optionally substituted alkoxy preferably having 1 to about 10 carbon atoms; optionally substituted alkylthio preferably having 1 to about 10 carbon atoms; optionally substituted alkylsulfinyl preferably 1 to about 10 carbon atoms; optionally substituted alkylsulfonyl preferably having 1 to about 10 carbon atoms; optionally substituted carboxy preferably have 1 to about 10 carbon atoms (which includes groups such as —COOR' where R' is H or $C_{1-8}$alkyl, including esters that are substantially non-reactive with photoacid); a photoacid-labile group such as a photoacid-labile ester e.g. a tert-butyl ester and the like; etc.

m is 1 (to provide a fused five-membered ring), 2 (to provide a fused six-membered ring), 3 (to provide a fused seven-membered ring), or 4 (to provide a fused eight-membered ring);

n is an integer of from 0 (i.e. no R ring substituents), 1 (i.e. a single R ring substituent) to the maximum possible value permitted by the valences of the ring members, and preferably n is 0, 1, 2, 3, 4 or 5, and more preferably n is 0, 1, 2 or 3;

p is the mole fraction of the fused oxygen ring units based on total units in the polymer; and r is the mole fraction of the fused carbon alicyclic ring units based on total units in the polymer, and p is greater than zero and r is zero (where the fused carbon alicyclic group is absent) or greater than zero (where the fused carbon alicyclic group is present in the polymer).

As referred to herein, the term "alkyl" is intended to include both branched and straight-chain saturated aliphatic hydrocarbon groups as well as alicyclic groups. Examples of alkyl include methyl, ethyl, n-propyl, i-propyl, n-butyl, s-butyl, t-butyl, n-pentyl, and s-pentyl. Preferred alkyl groups are $C_1$-$C_{22}$ alkyl groups. An alkyl group includes cyclic structures and may contain a multiple carbon-carbon bond provide the group is not aromatic (i.e. the term alkyl includes alicyclic, alkenyl and alkynyl).

As discussed above, references to a "quaternary" carbon indicate the carbon atom has four non-hydrogen substituents (i.e. $CRR^1R^2R^3$ where R, $R^1$, $R^2$ and $R^3$ are each the same or different and each is other than hydrogen). See, for instance, Morrison and Boyd, Organic Chemistry, particularly at page 85 ($3^{rd}$ ed., Allyn and Bacon), for a discussion of those term quaternary. In the case of photoacid-labile esters of compounds and polymers of the invention, it is often preferred that a quaternary carbon is directly linked (i.e. covalently linked with no other interpose atoms) to the ester carboxyl oxygen, i.e. linked to the underlined oxygen of the ester group: —<u>O</u>C(=O)—.

As used herein, "heteroalkyl" is intended to include branched, straight-chain and cyclic saturated aliphatic hydrocarbon groups including alkylene, having the specified number of carbon atoms and at least one heteroatom, e.g., N, O or S. Heteroalkyl groups will typically have between about 1 and 20 carbon atoms and about 1, 2 or 3 heteroatoms, preferably about 1 to 8 carbon atoms Preferred heteroalkyl groups include the following groups. Preferred alkylthio groups include those groups having one or more thioether linkages and from 1 to 12 carbon atoms, more preferably from 1 to 6 carbon atoms. Preferred alkylsulfinyl groups include those groups having one or more sulfoxide (SO) groups and from 1 to 12 carbon atoms, more preferably from 1 to 6 carbon atoms. Preferred alkylsulfonyl groups include those groups having one or more sulfonyl ($SO_2$) groups and from 1 to 2 carbon atoms, more preferably from 1 to 6 carbon atoms. Preferred alkoxy group have one or more ether linkages and 1 to 12 carbon atoms, more preferably from 1 to 6 carbon atoms. Preferred aminoalkyl groups include those groups having one or more primary, secondary and/or tertiary amine groups, and from 1 to 12 carbon atoms, more preferably from 1 to 6 carbon atoms.

References herein to a cyanoalkyl group or cyanoheteoalkyl group indicate an alkyl or heteroalkyl group as specified above, having cyano group substituent at one or more available positions. A cyanoalkyl or cyanoheteroalkyl group typically has one, two or three cyano moieties, more typically one or two cyano moieties.

As discussed, various moieties may be optionally substituted, including groups of Formulae I, II, IIa, III, IIIa, IV and IVa and polymers that contain polymerized units of compounds of those formulae, including polymers of Formula V and VI above. A "substituted" substituent may be substituted at one or more available positions, typically 1, 2, or 3 positions by one or more suitable groups such as e.g. cyano; $C_{1-8}$ alkyl; $C_{1-8}$ alkoxy; $C_{1-8}$ alkylthio; $C_{1-8}$ alkylsulfonyl; $C_{2-8}$ alkenyl; $C_{2-8}$ alkynyl; hydroxyl; nitro; alkanoyl such as a $C_{1-6}$ alkanoyl e.g. acyl and the like; etc. Less preferred for many applications will be fluoro other halogen substitution as discussed above and such halogen substitution is at least substantially excluded in certain embodiments, as discussed above.

Syntheses of Compounds and Polymers

Compounds and polymers of the invention can be readily prepared. For instance, various adamantyl reagents are commercially available e.g. 1-hydroxyadamantane, 2-hydroxyadamantane, 2-adamantanone, 1-adamanataneacetic acid, 1-adamantanecarboxylic acid, 1-adamantane acetic acid, and 1,3-adamantanedicarboxylic acid.

Such compounds can be functionalized to provide a polymerizable cyanoacrylate compound. For instance, cyanomethylbromide ($CNCH_2Br$) can be reacted with Mg to form the Grignard reagent which is reacted with 2-adamantanone to provide 2-methylcyano-2-hydroxy-adamantyl. That methylcyano-hydroxy-adamantyl compound can be reacted with methacryloyl chloride to provide a compound of Formula II as defined above where R is hydrogen, $R^1$ is methyl and $R^3$ is —$CH_2CN$, i.e. 2-cyanomethyl-2-adamantyl methacrylate. Similarly, the methylcyano-hydroxy-adamantyl compound can be reacted with acryloyl chloride to provide a compound of Formula II as defined above where R and $R^1$ are each hydrogen and $R^3$ is —$CH_2CN$.

3-Hydroxy-1-adamantane carbonitrile can be prepared by known procedures, e.g. as disclosed in *Russian Journal of General Chemistry* (Translation of Zhurnal Obshchei Khimii) (2001), 71(7),1121-1125. That compound also can be reacted with methacryloyl chloride or acryloyl chloride to provide the corresponding 1-3-cyano-adamantyl acrylate esters.

Other cyanoadamantyl reagents are disclosed in K. Petrov et al. *Zhurnal Organicheskoi Khimii* (1992), 28(1), 129-32; and R. Bielmann et al. *Helvetica Chimica Acta* (1982), 65(6), 1728-33.

Polymers of the invention can be prepared by a variety of methods. One suitable method is an addition reaction which may include free radical polymerization, e.g., by reaction of selected monomers to provide the various units as discussed above in the presence of a radical initiator under an inert atmosphere (e.g., $N_2$ or argon) and at elevated temperatures such as about 70° C. or greater, although reaction temperatures may vary depending on the reactivity of the particular reagents employed and the boiling point of the reaction solvent (if a solvent is employed). Suitable reaction solvents include e.g. tetrahydrofuran, ethyl lactate and the like. Suitable reaction temperatures for any particular system can be readily determined empirically by those skilled in the art based on the present disclosure. A variety of free radical initiators may be employed. For example, azo compounds may be employed such as azo-bis-2,4-dimethylpentanenitrile. Peroxides, peresters, peracids and persulfates also could be employed.

Other monomers that can be reacted to provide a polymer of the invention can be identified by those skilled in the art. For example, to provide photoacid-labile units, suitable monomers include e.g. methacrylate or acrylate that contains the appropriate group substitution (e.g. tertiary alicyclic, t-butyl, etc.) on the carboxy oxygen of the ester group. Maleic anhydride is a preferred reagent to provide fused anhydride polymer units. Itaconic anhydride also is a preferred reagent to provide anhydride polymer units, preferably where the itaconic anhydride has purified such as by extraction with chloroform prior to polymerization. Vinyl lactones are also preferred reagents, such as alpha-butyrolactone.

Some suitable vinyl (endocyclic double bond) heterocyclic monomers that can be polymerized to provide polymers of the invention include the following:

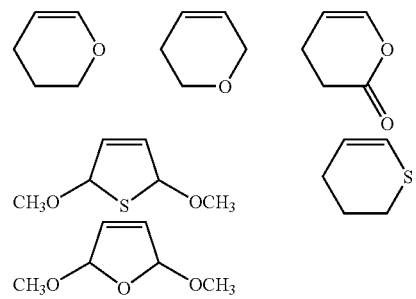

Suitably, a polymer of the invention will contain at least about 1 or 5 mole percent cyanoadamantyl groups based on total polymer units, more preferably at least about 10, 15, 20, 25, 30 or 40 mole percent cyanoadamantyl groups based on total polymer units.

Preferably a polymer of the invention will have a weight average molecular weight (Mw) of about 800 or 1,000 to about 100,000, more preferably about 2,000 to about 30,000, still more preferably from about 2,000 to 15,000 or 20,000, with a molecular weight distribution (Mw/Mn) of about 3 or less, more preferably a molecular weight distribution of about 2 or less. Molecular weights (either Mw or Mn) of the polymers of the invention are suitably determined by gel permeation chromatography.

Photoresist Compositions

Polymers of the invention used in positive photoresist formulations should contain a sufficient amount of photogenerated acid labile ester or acetal groups or other contrasting-enhancing groups to enable formation of resist relief images as desired. For instance, suitable amount of such acid labile ester groups will be at least 1 mole percent of total units of the polymer, more preferably about 2 to 50 mole percent, still more typically about 3 to 20, 30 or 40 mole percent of total polymer units. See the examples which follow for exemplary preferred polymers.

As discussed above, the polymers of the invention are highly useful as a resin binder component in photoresist compositions, particularly chemically-amplified positive resists. Photoresists of the invention in general comprise a photoactive component and a resin binder component that comprises a polymer as described above.

The resin component should be used in an amount sufficient to render a coating layer of the resist developable with an aqueous alkaline developer.

The resist compositions of the invention also comprise a photoacid generator (i.e. "PAG") that is suitably employed in an amount sufficient to generate a latent image in a coating layer of the resist upon exposure to activating radiation. Preferred PAGs for imaging at 193 nm and 248 nm imaging include imidosulfonates such as compounds of the following formula:

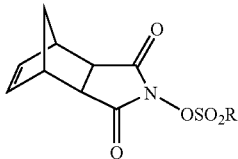

wherein R is camphor, adamantane, alkyl (e.g. $C_{1-12}$ alkyl) and perfluoroalkyl such as perfluoro($C_{1-12}$alkyl), particularly perfluorooctanesulfonate, perfluorononanesulfonate and the like. A specifically preferred PAG is N-[(perfluorooctanesulfonyl)oxy]-5-norbornene-2,3-dicarboximide.

Sulfonate compounds are also suitable PAGs, particularly sulfonate salts. Two suitable agents for 193 nm and 248 nm imaging are the following PAGS 1 and 2:

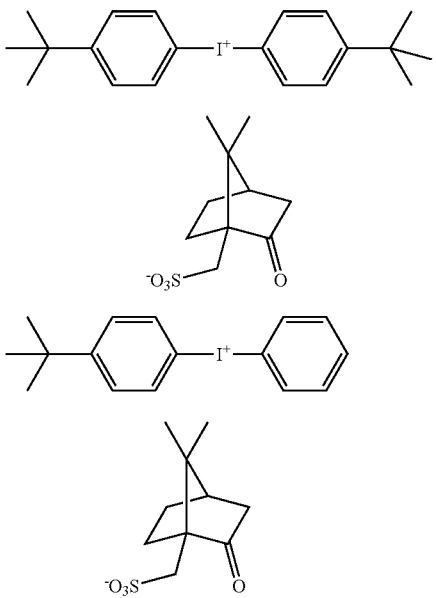

Such sulfonate compounds can be prepared as disclosed in European Patent Application 96118111.2 (publication number 0783136), which details the synthesis of above PAG 1.

Also suitable are the above two iodonium compounds complexed with anions other than the above-depicted camphorsulfonate groups. In particular, preferred anions include those of the formula $RSO_3-$ where R is adamantane, alkyl (e.g. $C_{1-12}$ alkyl) and perfluoroalkyl such as perfluoro ($C_{1-12}$alkyl), particularly perfluorooctanesulfonate, perfluorobutanesulfonate and the like.

Other known PAGS also may be employed in the resists of the invention. Particularly for 193 nm imaging, generally preferred are PAGS that do not contain aromatic groups, such as the above-mentioned imidosulfonates, in order to provide enhanced transparency.

A preferred optional additive of resists of the invention is an added base, particularly tetrabutylammonium hydroxide (TBAH), or tetrabutylammonium lactate, which can enhance resolution of a developed resist relief image. For resists imaged at 193 nm, a preferred added base is a hindered amine such as diazabicyclo undecene or diazabicyclononene. The added base is suitably used in relatively small amounts, e.g. about 0.03 to 5 percent by weight relative to the total solids.

Photoresists of the invention also may contain other optional materials. For example, other optional additives include anti-striation agents, plasticizers, speed enhancers, etc. Such optional additives typically will be present in minor concentrations in a photoresist composition except for fillers and dyes which may be present in relatively large concentrations, e.g., in amounts of from about 5 to 30 percent by weight of the total weight of a resist's dry components.

The resists of the invention can be readily prepared by those skilled in the art. For example, a photoresist composition of the invention can be prepared by dissolving the components of the photoresist in a suitable solvent such as, for example, ethyl lactate, ethylene glycol monomethyl ether, ethylene glycol monomethyl ether acetate, propylene glycol monomethyl ether; propylene glycol monomethyl ether acetate and 3-ethoxyethyl propionate. Typically, the solids content of the composition varies between about 5 and 35 percent by weight of the total weight of the photoresist composition. The resin binder and photoactive components should be present in amounts sufficient to provide a film coating layer and formation of good quality latent and relief images. See the examples which follow for exemplary preferred amounts of resist components.

The compositions of the invention are used in accordance with generally known procedures. The liquid coating compositions of the invention are applied to a substrate such as by spinning, dipping, roller coating or other conventional coating technique. When spin coating, the solids content of the coating solution can be adjusted to provide a desired film thickness based upon the specific spinning equipment utilized, the viscosity of the solution, the speed of the spinner and the amount of time allowed for spinning.

The resist compositions of the invention are suitably applied to substrates conventionally used in processes involving coating with photoresists. For example, the composition may be applied over silicon wafers or silicon wafers coated with silicon dioxide for the production of microprocessors and other integrated circuit components. Aluminum-aluminum oxide, gallium arsenide, ceramic, quartz, copper, glass substrates and the like are also suitably employed.

Following coating of the photoresist onto a surface, it is dried by heating to remove the solvent until preferably the photoresist coating is tack free. Thereafter, it is imaged through a mask in conventional manner. The exposure is sufficient to effectively activate the photoactive component of the photoresist system to produce a patterned image in the resist coating layer and, more specifically, the exposure energy typically ranges from about 1 to 100 mJ/cm$^2$, dependent upon the exposure tool and the components of the photoresist composition.

As discussed above, coating layers of the resist compositions of the invention are preferably photoactivated by a short exposure wavelength, particularly a sub-300 and sub-200 nm exposure wavelength. As discussed above, 193 nm is a particularly preferred exposure wavelength. However, the resist compositions of the invention also may be suitably imaged at higher wavelengths.

Following exposure, the film layer of the composition is preferably baked at temperatures ranging from about 70° C. to about 160° C. Thereafter, the film is developed. The exposed resist film is rendered positive working by employing a polar developer, preferably an aqueous based developer such as quaternary ammonium hydroxide solutions such as a tetra-alkyl ammonium hydroxide solution; various amine solutions preferably a 0.26 N tetramethylammonium hydroxide, such as ethyl amine, n-propyl amine, diethyl amine, di-n-propyl amine, triethyl amine, or methyldiethyl amine; alcohol amines such as diethanol amine or triethanol amine; cyclic amines such as pyrrole, pyridine, etc. In general, development is in accordance with procedures recognized in the art.

Following development of the photoresist coating over the substrate, the developed substrate may be selectively processed on those areas bared of resist, for example by chemically etching or plating substrate areas bared of resist in accordance with procedures known in the art. For the manufacture of microelectronic substrates, e.g., the manufacture of silicon dioxide wafers, suitable etchants include a gas etchant, e.g. a halogen plasma etchant such as a chlorine or fluorine-based etchant such a Cl$_2$ or CF$_4$/CHF$_3$ etchant applied as a plasma stream. After such processing, resist may be removed from the processed substrate using known stripping procedures.

All documents mentioned herein are incorporated herein by reference. The following non-limiting examples are illustrative of the invention.

EXAMPLES 1-2

Syntheses of Cyanoadamantyl Monomers

EXAMPLE 1

Synthesis of 2-cyanomethyl-2-adamantyl methacrylate [Formula II: R=H; R$^1$=CH$_3$; R$^3$=—CH$_2$CN ].

A three-neck flask under nitrogen is charged with 100 mL toluene and 1 gm of cyanomethylbromide (CNCH$_2$Br) and cooled with an ice bath. A slight molar excess of Mg is added to the toluene and the mixture stirred until completion of formation of the Grignard reagent. A molar equivalent of 2-adamantanone is then added to the reaction mixture and stirring continued for 30 minutes or more while warming to room temperature. The reaction mixture is then again cooled with an ice bath and a slight molar excess of methacrylol chloride is added dropwise. When the acid chloride addition is complete, the ice bath is removed and stirring continued at room temperature until reaction completion. The resulting 2-cyanomethyl-2-adamantyl methacrylate can be isolated and purified by extraction and/or chromatography.

EXAMPLE 2

Synthesis of 3-cyano-adaman-1-yl methacrylate [Formula III: R=H; R$^1$=CH$_3$; R$^3$=—CN].

3-Hydroxy-1-adamantane carbonitrile is prepared as disclosed in Russian Journal of General Chemistry (2001),71 (7),1121-1125. The procedures of Example 1 above are generally followed to form the acrylate ester of 3-hydroxy-1-adamantane carbonitrile and produce the title compound. Thus, a three-neck flask under nitrogen is charged with 100 mL toluene and 1 gm of 3-hydroxy-1-adamantane carbonitrile and cooled with an ice bath. A slight molar excess of methacrylol chloride is added dropwise. When the acid chloride addition is complete, the ice bath is removed and stirring continued at room temperature until reaction completion. The resulting 3-cyano-adaman-1-yl methacrylate can be isolated and purified by extraction and/or chromatography.

EXAMPLES 3-8

Syntheses of Cage and Lactone Monomers Useful in Polymers of the Invention

EXAMPLE 3

Synthesis of Ethyl Fenchol Methacrylate

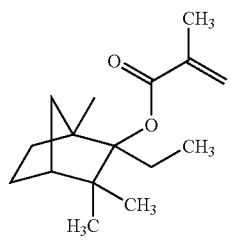

Materials Used:

| | Amount Charged | moles | Source |
|---|---|---|---|
| Ethyl fenchol | 182.31 g | 1.00 | Aldrich |
| n-BuLi (2.5 M in hexanes) | 440 mL | 1.10 | Aldrich |
| Methacryloyl chloride | 112.4 mL | 1.15 | Aldrich, distilled before use |
| THF anhydrous | 600 mL | | Aldrich, degassed before use |

Procedure:

All reaction glassware and needles were dried and flushed with dry N$_2$ before use and the reaction was carried out under nitrogen atmosphere.
1) Into a 2 L 3-neck RBF equipped with an addition funnel and a magnetic stirrer were added 182.31 g of 2-Ethyl fenchol and 600 mL of anhydrous THF. The resulting colorless solution was cooled with an ice-water bath.
2) A n-BuLi solution (440 mL) was transferred to the addition funnel via a double-tipped needle and then added to the cooled THF solution over 30 min. When added, the resulting yellowish solution was kept in the ice-water bath and stirred for 2 h.

3) Methacryloyl chloride (112.4 mL, 104.54 g) was added dropwise over 20 min. The resulting yellow suspension was allowed to warm to room temperature and stirred overnight.
4) The LiCl salts were filtered off. The filtrate was cooled in an ice-water bath while 200 mL of pre-cooled DI water was added. The resulting solution was stirred for 1.5 h and the organic phase was isolated (some ether or THF may be added to assist extraction), washed with DI water (2×200 mL), then saturated Na$_2$CO$_3$ solution (2×200 mL), then DI water (3×200 mL) again, and dried over anhydrous MgSO$_4$.
5) The slightly yellow solution was concentrated on a rotary evaporator (bath temperature kept below 35°) to yield a clear slightly yellow liquid product. Yield >90%.
6) The crude EFMA may be purified to remove the yellow color plus methacrylic anhydride impurity via flash filtration through pre-conditioned silica (using hexanes) in Buchner. The monomer is eluted with hexanes only and comes through in the early eluting fractions as a colorless liquid when rotovapped. The product was judged pure by NMR.

EXAMPLE 4

2-Methyl-2-adamantyl methacrylate

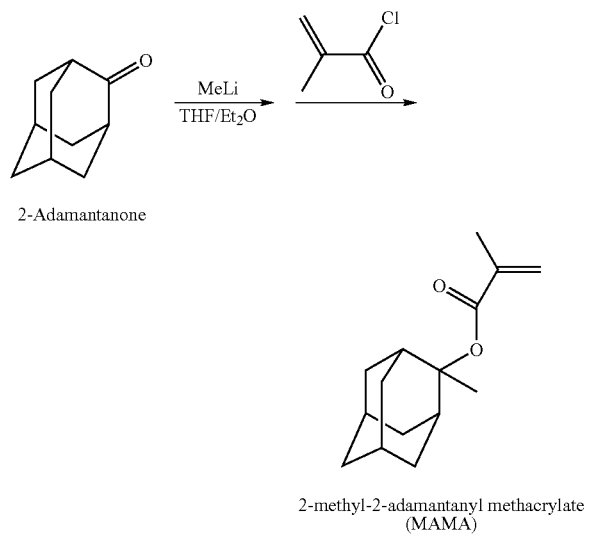

2-methyl-2-adamantanyl methacrylate
(MAMA)

Materials Used:

|  | Amount Charged | moles | Source |
| --- | --- | --- | --- |
| 2-Adamantanone | 150.22 g | 1.00 | Lancaster |
| MeLi (1.4 M in Ether) | 786 mL | 1.10 | Aldrich |
| Methacryloyl chloride | 112.4 mL | 1.15 | Aldrich, distilled before use |
| THF anhydrous | 600 mL |  | Aldrich, degassed before use |

Procedure:

All reaction glassware and needles were dried and flushed with dry N$_2$ before use and the reaction was carried out under nitrogen atmosphere.

1) A Methyllithium solution (786 mL) was transferred via a double-tipped needle to a 2 L 3-neck RBF equipped with an addition funnel and a magnetic stirrer, and cooled with an ice-water bath.
2) 2-Adamantanone (150.22 g) was dissolved (over 0.5 h) in anhydrous THF (600 mL) and the resulting colorless solution was transferred to the addition funnel via a double-tipped needle and then added to the cooled MeLi solution over 30 min. When added, the resulting white suspension was allowed to warm to room temperature and stirred for 2 h.
3) The white suspension then was cooled using an ice-water bath and methacryloyl chloride (112.4 mL, 104.54 g) was added dropwise over 20 min. The white solid faded out and a new white (LiCl) suspension formed. The resulting white suspension was allowed to warm to room temperature and stirred overnight.
4) The LiCl salts were filtered off. The filtrate was cooled in an ice-water bath while 200 mL of pre-cooled DI water was added. The resulting solution was stirred for 1.5 h and the organic phase was isolated (some ether or THF may be added to assist extraction), washed with DI water (2×200 mL), then saturated Na$_2$CO$_3$ solution (2×200 mL), then DI water (3×200 mL) again, and dried over anhydrous MgSO$_4$.
5) The slightly yellow solution was concentrated on a rotary evaporator (bath temperature kept below 35°) to yield a clear slightly yellow liquid product. Yield >90%.
6) The crude MAMA may be purified to remove the yellow color plus methacrylic anhydride impurity via flash filtration through pre-conditioned silica (using hexanes) in Buchner. The monomer is eluted with hexanes only and comes through in the early eluting fractions as a colorless liquid when rotovapped. The product was judged pure by NMR.

EXAMPLE 5

Synthesis of 8-methyltricyclodecanyl methacrylate

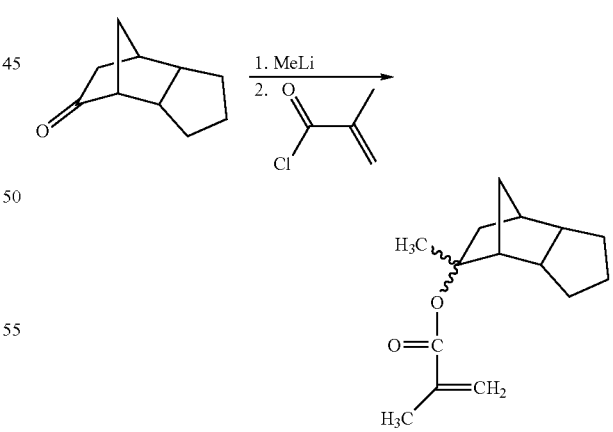

A solution of 125 ml of 1.4 M methyl lithium (in ethyl ether) in 100 ml of hexane was decanted into a three neck round-bottom flask at an ice-water bath. To it, a solution of 24.00 g of tricyclo[5.2.1.0]decan-8-one in hexane was added dropwise. After addition, the reaction mixture was stirred for 4 hours at 0° C. Then, a solution of 16 ml of methacroyl chloride in 100 ml of hexane was added dropwise at 0° C.

After addition, the reaction mixture was stirred at the same bath for overnight (16 hours). After filtering the white salts, the organic layer was washed with water three times (3×300 ml). Then, the washed organic layer was dried over anhydrous MgSO$_4$. The organic solvent was removed by a rotary pump to give the crude title monomer (23.5 g). The monomer was purified by a flash column chromatography (purity >98%, silica gel with hexane). $^1$H NMR: 6.05 (1H), 5.50 (1H), 1.95 (3H), 1.65 (3H), 2.25-0.85 (14H).

EXAMPLE 6

Synthesis of tetrahydro-2-oxo-2-H-furan-4-yl methacrylate

The methacrylate monomer, tetrahydro-2-oxo-2-H-furan-4-yl methacrylate was synthesized in one step esterification from commercially available compound. A mixture of (S)-(−)-(α-hydroxy-(-butyrolactone (41.77 g, 0.419 mole) and triethylamine (45.32 g, 0.449 mole) in 100 mL of dry THF was placed in a three-neck round-bottom flask under a dry nitrogen atmosphere at an ice-water bath. To it, a solution of distilled methacryloyl chloride (45 mL, 0.461 mole) in 200 ML of dry THF was added slowly (about 1 hour). During the addition, white precipitation (triethylamine salt) was observed in the reaction mixture. The reaction mixture was stirred over night (about 18 hour). The resultant mixture was filtered, and the filtrate was concentrated by a rotary pump. The concentrated mixture was added 500 mL of ethyl acetate and washed with water (2×500 mL) twice. The organic layer was dried with anhydrous MgSO$_4$ and concentrated by a rotary pump. The purification of the crude monomer by column chromatography (neutral aluminum oxide, 300 g, hexane, then hexane/EtoAc=1/1). The purity of the monomer is about 95% (by NMR) and 52% yield. $^1$H NMR (CDCl$_3$,ppm): 6.20 (1H), 5.70 (1H), 5.55 & 4.95 (1 H), 4.55 (dd, 1H), 4.4 (d, 1H), 2.90 (dd, 1H), 2.70 (d, 1H), 1.95 (3H). $^{13}$C NMR (CDCl$_3$,ppm): 174.1, 166.5, 135.5, 126.8, 72.9, 70.0, 34.5, 17.9.

EXAMPLE 7 alpha-Butyrolactone Methacrylate Synthesis

To a 250 ml 3N-RB flask fitted with a gas inlet, thermometer, overhead stirrer and a 125 ml pressure equalizing dropping funnel was added 26.5 g triethylamine. The triethylamine was cooled to 5° C. using a water/ice bath. Once the triethylamine was at 5° C. the methacrylic acid was added dropwise over a 20-25 min period. The mixture exothermed ~10 C. After the addition was complete the water/ice bath was removed. While the solution was stirring (20 min) the dropping funnel was removed and replaced with a clean 125 ml pressure equalizing dropping funnel. The bromolactone (41.25 g)/THF (62.5 ml) was added dropwise over a 30 min. The mixture warmed from ~18° C. to ~30° C. with a precipitate forming. The reaction was heated to 55° C. and held at 55° C. for 16 hrs using an oil bath/hot plate. After heating for 16 hrs the mixture was cooled to 20° C. using a water/ice bath. The solid (44.5 g) was removed by vacuum filtration. The filtrates were reduced under partial pressure at 33-34° C. The resulting dark amber/brown oil was diluted with 90 g of methylene chloride. This solution was slowly poured onto a plug of silica gel (180 g, Baker 40 um flash chromatography packing) which had been pre-conditioned with methylene chloride. The crude mixture was allowed to pass into the silica gel plug by gravity. Once the crude mixture had passed the surface of the silica gel plug a fresh portion of methylene chloride was slowly poured onto the plug. The methylene chloride was pulled through the silica gel plug using reduced pressure. Once the methylene chloride had passed the surface of the silica gel plug the vacuum was removed then the next portion of methylene chloride was slowly poured onto the plug. This procedure was followed until all the product was extracted. The total filtrate was 850 ml. [The product was detected by spotting an aliquot on a TLC plate then illuminating with short UV.] To the orange filtrate was added 36 g of activated charcoal. The mixture was stirred for 1.5 hrs then filtered through a Celite plug (pre-conditioned with methylene chloride). The charcoal/Celite was washed with (2×100 ml, 1×50 ml methylene chloride). The filtrate was then washed with 2×200 ml D.I. water. The layers were separated and the organic layer was dried over 100 g of sodium sulfate. The mixture was stirred for 15-30 min. The sodium sulfate was removed and washed with 2×50 ml methylene chloride. The pale yellow filtrate (1.2 L) was stripped under reduced pressure at 33-34° C. leaving 36.4 g of a pale orange oil, Yield 85.6%.

EXAMPLE 8

Synthesis of pinanyl methacrylate

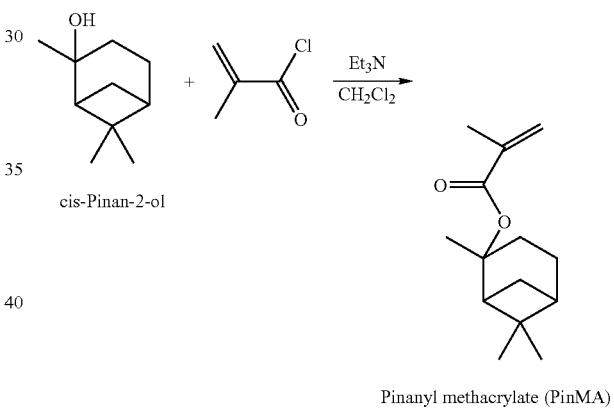

Pinanyl methacrylate (PinMA)

Materials Used:

| | Amount Charged | Moles | Source |
| --- | --- | --- | --- |
| cis-Pinan-2-ol | 15.43 g | 0.10 | Fluka |
| Et$_3$N | 12.14 g | 0.12 | Aldrich, distilled before use |
| Methacryloyl chloride | 13.07 g | 0.125 | Aldrich, distilled before use |
| CH$_2$Cl$_2$ | 230 mL | | Aldrich, dried and distilled |

Procedure:
  All reaction glassware and needles were dried and flushed with dry N$_2$ before use and the reaction was carried out under nitrogen atmosphere.
1) Into a 500 mL 3-neck round-bottom-flask equipped with an addition funnel and a magnetic stirrer were added 15.43 g of cis-pinan-2-ol and 200 mL of dry CH$_2$Cl$_2$ (Stirred over CaH$_2$ overnight, then distilled and stored over activated molecular sieves). The resulting colorless solution was cooled with an ice-water bath.

2) Triethylamine (12.14 g) was added through the addition funnel to the cooled CH$_2$Cl$_2$ solution over 10 min. After added, the resulting solution was kept in a dry-ice/acetone bath (−67° C.).
3) A CH$_2$Cl$_2$ (30 mL) solution of methacryloyl chloride (13.07 g) was added dropwise over 20 min. The resulting orangish suspension was allowed to warm to room temperature and stirred for 2 h.
4) The chloride salts were filtered off. The filtrate was washed with saturated Na$_2$CO$_3$ solution (2×200 mL), then DI water (3×200 mL), and dried over anhydrous MgSO$_4$.
5) The slightly yellow CH$_2$Cl$_2$ solution was concentrated on a rotary evaporator (bath temperature kept below 35°) to yield a clear slightly yellow liquid product. Yield=79%. The product was judged pure by NMR.

EXAMPLE 9-12

Polymer Synthesis

The following monomers were employed in the syntheses of Examples 9, 10, 11 and 12.

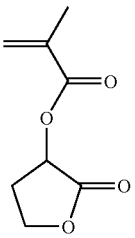

2-Methyl-acrylic acid
2-oxo-tetrahydro-furan-3-yl ester
(α-GBLMA)

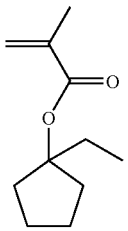

2-Methyl-acrylic acid
1-ethyl-cyclopentyl ester
(ECPMA)

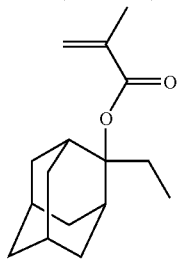

2-Methyl-acrylic acid
2-ethyl-adamantan-2-yl ester
(EAMA)

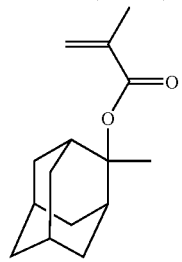

2-Methyl-acrylic acid
2-mthyl-adamantan-2-yl ester
(MAMA)

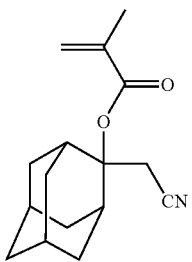

2-Methyl-acrylic acid
2-cyanomethyl-adamantan-2-yl ester
(CMAMA)

Maleic anhydride
(MA)

Norbornene
(NB)

EXAMPLE 9

Synthesis of ECPMA/α-GBLMA/CMAMA terpolymer 15.12 g of 2-methyl-acrylic acid 1-ethyl-cyclopentyl ester (ECPMA), 14.12 g of 2-methyl-acrylic acid 2-oxo-tetrahydro-furan-3-yl ester (α-GBLMA), and 10.76 g of 2-methyl-acrylic acid 2-cyanomethyl-adamantan-2-yl ester (CMAMA) were dissolved in 40 mL of THF. The mixture was degassed by bubbling with nitrogen for 20 min. 2.39 g of V601 (dimethyl-2,2-azodiisobutyrate, 5 mol % with respect to monomers) was dissolved in 20 mL of THF and charged into a 250 mL flask, equipped with a nitrogen inlet and a condenser. After degassing the V601 solution by bubbling with nitrogen for 20 min, the reactor containing V601 solution was placed in an oil bath kept at 75° C. and the monomer solution was fed into the reactor at a rate of 0.444 mL/min. The monomer feeding was carried out for 3 hours. After monomer feeding was complete, the polymerization mixture was stirred for additional 1 hour at 75° C. After a total of 4 hour polymerization time (3 hour feeding and 1 hour stirring), the polymerization mixture was cooled down to room temperature. Precipitation was carried out in a 1.5 L of isopropyl alcohol. After filtration, the polymer was dried, re-dissolved in 50 g of THF, reprecipitated into 1.5 L of isopropyl alcohol, filtered, and dried in a vacuum oven at 50° C. for 48 hours to give 30.98 g (Mw=13,066 and Mw/Mn=~2.02).

EXAMPLE 10

Synthesis of EAMA/α-GBLMA/CMAMA terpolymer 18.12 g of EAMA, 12.42 g of α-GBLMA, and 9.46 g of CMAMA were dissolved in 40 mL of THF. The mixture was degassed by bubbling with nitrogen for 20 min. 2.1 g of V601 (dimethyl-2,2-azodiisobutyrate, 5 mol % with respect to monomers) was dissolved in 20 mL of THF and charged into a 250 mL flask, equipped with a nitrogen inlet and a condenser. After degassing the V601 solution by bubbling with nitrogen for 20 min, the reactor containing V601 solution was placed in an oil bath kept at 75° C. and the monomer solution was fed into the reactor at a rate of 0.444 mL/min. The monomer feeding was carried out for 3 hours. After monomer feeding was complete, the polymerization mixture was stirred for additional 1 hour at 75° C. After a total of 4 hour polymerization time (3 hour feeding and 1 hour stirring), the polymerization mixture was cooled down to room temperature. Precipitation was carried out in a 1.5 L of isopropyl alcohol. After filtration, the polymer was dried, re-dissolved in 50 g of THF, reprecipitated into 1.5 L of isopropyl alcohol, filtered, and dried in a vacuum oven at 50° C. for 48 hours to give 24.32 g (Mw=11,370 and Mw/Mn=~1.99).

EXAMPLE 11

Synthesis of MAMA/α-GBLMA/CMAMA terpolymer 17.55 g of MAMA, 12.74 g of α-GBLMA, and 9.71 g of CMAMA were dissolved in 40 mL of THF. The mixture was degassed by bubbling with nitrogen for 20 min. 2.16 g of V601 (dimethyl-2,2-azodiisobutyrate, 5 mol % with respect to monomers) was dissolved in 20 mL of THF and charged into a 250 mL flask, equipped with a nitrogen inlet and a condenser. After degassing the V601 solution by bubbling with nitrogen for 20 min, the reactor containing V601 solution was placed in an oil bath kept at 75° C. and the monomer solution was fed into the reactor at a rate of 0.444 mL/min. The monomer feeding was carried out for 3 hours. After monomer feeding was complete, the polymerization mixture was stirred for additional 1 hour at 75° C. After a total of 4 hour polymerization time (3 hour feeding and 1 hour stirring), the polymerization mixture was cooled down to room temperature. Precipitation was carried out in a 1.5 L of isopropyl alcohol. After filtration, the polymer was dried, re-dissolved in 50 g of THF, reprecipitated into 1.5 L of isopropyl alcohol, filtered, and dried in a vacuum oven at 50° C. for 48 hours to give 28.87 g (Mw=12,440 and Mw/Mn=~1.40).

EXAMPLE 12

Synthesis of ECPMA/CMAMA/MA/NB tetrapolymer 14.15 g of ECPMA, 13.42 g of CMAMA, 6.34 g of maleic anhydride (MA), and 6.09 g of norbornene (NB) were dissolved in 40 mL of THF. The mixture was degassed by bubbling with nitrogen for 20 min. 1.19 g of V601 (dimethyl-2,2-azodiisobutyrate, 5 mol % with respect to monomers) was dissolved in 20 mL of THF and charged into a 250 mL flask, equipped with a nitrogen inlet and a condenser. After degassing the V601 solution by bubbling with nitrogen for 20 min, the reactor containing V601 solution was placed in an oil bath kept at 75° C. and the monomer solution was fed into the reactor at a rate of 0.444 mL/min. The monomer feeding was carried out for 3 hours. After monomer feeding was complete, the polymerization mixture was stirred for additional 1 hour at 75° C. After a total of 4 hour polymerization time (3 hour feeding and 1 hour stirring), the polymerization mixture was cooled down to room temperature. Precipitation was carried out in a 1.5 L of isopropyl alcohol. After filtration, the polymer was dried, re-dissolved in 50 g of THF, precipitated into 1.5 L of isopropyl alcohol, filtered, and dried in a vacuum oven at 50° C. for 48 hours to give 18.80 g (Mw=10,660 and Mw/Mn=~1.86).

EXAMPLE 13

Preparation of a Photoresist of the Invention

A resist of the invention is prepared by admixing the following components in the following amounts:

| Component | Amount |
|---|---|
| Resin | 7.6 wt. % of formulation |
| PAG | 5.2 wt. % of resin |
| Basic Additive | 0.24 wt. % of resin |
| Surfactant | 0.1 wt. % of resin |
| Solvent | to provide 92 wt. % fluid fomulation |

In the resist, the resin is a polymer of Example 9 above. The PAG is triphenylsulfonium perfluorobutane sulfonate. The basic additive is tetrabutylammonium lactate. The surfactant is R08 (commercial name MEGAFAC R-08, a fluoroacrylate ester copolymer). The solvent is 2-heptanone.

The formulated resist composition is spin coated onto HMDS vapor primed 4 inch silicon wafers and softbaked via a vacuum hotplate at 120° C. for 90 seconds. The resist coating layer is exposed through a photomask at 193 nm, and then the exposed coating layers are post-exposure baked at 100° C. The imaged resist layer is then developed by treatment with an aqueous tetramethylammonium hydroxide solution.

The foregoing description of the invention is merely illustrative thereof, and it is understood that variations and modification can be made without departing from the spirit or scope of the invention as set forth in the following claims.

What is claimed is:

1. A polymer that comprises an adamantyl moiety that comprises a cyano group at the 2 or 4 ring positions of the adamantyl moiety.

2. The polymer of claim 1 wherein the adamantyl moiety comprises a cyano group at the 2 ring position of the adamantly moiety.

3. The polymer of claim 1 wherein the adamantyl moiety comprises a cyano group at the 4 ring position of the adamantly moiety.

4. The polymer of claim 1 wherein the polymer is at least substantially free of aromatic groups.

5. The polymer of claim 1 wherein the polymer is at least substantially free of fluorine atoms.

6. The polymer of claim 1 wherein the polymer comprises photoacid-labile groups.

7. A polymer that comprises (i) phenolic groups and (ii) an adamantyl moiety that comprises a cyano group.

8. The polymer of claim 7 wherein the polymer is at least substantially free of fluorine atoms.

9. The polymer of claim 7 wherein the polymer comprises photoacid-labile groups.

10. A polymer that comprises an adamantyl moiety that comprises a cyano group at the 2 or 4 ring positions of the adamantyl moiety,
the polymer being at least substantially free of aromatic groups and fluorine atoms; and
the polymer comprising photoacid-labile groups.

11. The polymer of claim 10 wherein the adamantyl moiety comprises a cyano group at the 2 ring position of the adamantly moiety.

12. The polymer of claim 10 wherein the adamantyl moiety comprises a cyano group at the 4 ring position of the adamantly moiety.

* * * * *